US006274381B1

(12) United States Patent
Pauls et al.

(10) Patent No.: US 6,274,381 B1
(45) Date of Patent: Aug. 14, 2001

(54) METHOD FOR INVISIBLY TAGGING PETROLEUM PRODUCTS USING VISIBLE DYES

(75) Inventors: Theodore D. Pauls, Aurora; Susan I. Steuer, Chicago; Brian A. Foley, Aurora; Michael J. Denci, St. Charles, all of IL (US); Haresh Doshi, Somerville, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 1 day.

(21) Appl. No.: 09/188,639

(22) Filed: Nov. 9, 1998

(51) Int. Cl.[7] .................................................. G01N 37/00
(52) U.S. Cl. .............................. 436/56; 44/328
(58) Field of Search ................... 436/56; 44/328

(56) References Cited

U.S. PATENT DOCUMENTS

| 2,046,365 | | 7/1936 | Cassidy et al. . | |
|---|---|---|---|---|
| 3,862,120 | * | 1/1975 | Orelup | 260/191 |
| 3,883,568 | | 5/1975 | Turner et al. | 260/383 |
| 4,009,008 | | 2/1977 | Orelup | 44/59 |
| 4,209,302 | | 6/1980 | Orelup | 44/59 |
| 4,904,765 | | 2/1990 | Derber et al. | 534/573 |
| 5,225,679 | | 7/1993 | Clarke et al. | 250/343 |
| 5,525,516 | | 6/1996 | Krutak et al. | 436/56 |
| 5,663,386 | | 9/1997 | Raulfs et al. | 552/241 |
| 5,804,447 | | 9/1998 | Albert et al. | 436/56 |
| 5,984,983 | * | 11/1999 | Asgaonkar et al. | 44/385 |
| 5,998,211 | | 12/1999 | Albert et al. | 436/56 |

FOREIGN PATENT DOCUMENTS

| B-22357/88 | 2/1991 | (AU) . |
|---|---|---|
| 849 158 | 9/1952 | (DE) . |
| 0201368A1 | 11/1986 | (EP) . |
| 0481519A1 | 4/1992 | (EP) . |
| 0 656 929 | 5/1997 | (EP) . |
| 1001003A1 | 5/2000 | (EP) . |
| 1233793 | 5/1971 | (GB) . |

* cited by examiner

*Primary Examiner*—Jill Warden
*Assistant Examiner*—Monique T. Cole
(74) *Attorney, Agent, or Firm*—Kenneth Crimaldi

(57) ABSTRACT

This invention provides a method for invisibly tagging, for subsequent identification purposes, various liquid petroleum hydrocarbons, such as crude oil, diesel fuel, heating oil, kerosene, lubricating oils, waxes, jet fuel, and in particular gasoline, remarkably using visible dyes by incorporating therein one or more visible dyes at minute levels such that they cannot be visually detected by the human eye. Visible dyes which have high solubility in petroleum hydrocarbons and maximum absorption in the 550–700 nm visible wavelength range are used to impart such invisible markings. The visible dyes, although employed at non-visible levels, are still capable of detection in a relatively quick and simple manner which requires minimal instrumentation, creates no waste products for disposal, and gives true quantitative results of dye concentrations in the field. This invention, therefore, further provides a method for so identifying the tagged petroleum hydrocarbons by exposing the tagged hydrocarbon to visible light having wavelengths in the portion of the spectrum utilized and detecting and quantifying the presence of the dyes in the tagged product from their characteristic absorption with available absorption detection equipment sensitive in this spectral region. This invention also provides visible dye compositions particularly appropriate for said invisible tagging.

3 Claims, No Drawings ity and octane number, as well as to provide them with effective additive packages containing detergents and the like. Consumers rely upon the company's trademarks to assure themselves that the product being purchased is of high quality. Unscrupulous gasoline dealers can make large profits simply by diluting or substituting the brand name product with an inferior product and selling the resulting inferior product at the price consumers are willing to pay for the branded product. For example, it is possible for dealers to cheat by blending lower priced products such as kerosene, heating oil, or diesel fuel into regular grade gasoline or blending regular grade gasoline into higher priced premium gasoline and selling the inferior

METHOD FOR INVISIBLY TAGGING PETROLEUM PRODUCTS USING VISIBLE DYES

FIELD OF THE INVENTION

This invention is directed to a method for invisibly tagging petroleum products for identification purposes remarkably using visible dyes. The invention is also directed to a method for identifying the so tagged petroleum products and to visible dye compositions appropriate for said invisible tagging.

BACKGROUND OF THE INVENTION

It is well known that various liquid petroleum hydrocarbons, such as petroleum-derived fuels (e.g., gasoline, jet fuel, diesel fuel, heating oil, kerosene, lubricating oil) can be marked or tagged for identification purposes with visible dyes at dosage levels that impart a distinct color to the fuels perceptible to the human eye. Historically, yellow, red, blue, green, and purple solvent dyes, along with other solvent dyes that strongly absorb radiation in the visible portion of the electromagnetic spectrum, have been used as such fuel colorants.

The need to tag fuels to provide means to distinguish them from seemingly identical products exists for a number of reasons, including to identify various grades of fuels, to distinguish manufacturer's brands, to differentiate similar fuels taxed at different rates, and to make adulteration, counterfeiting, misuse, tax evasion, and theft impossible or at least traceable. The need primarily arises from differing price or tax structures of different fuels or even the same fuel used for different purposes and the opportunity in these situations for unscrupulous persons to cheat or abuse the tax laws.

For example, it is common for governments to require coloring of lower taxed fuels to provide means to distinguish them from similar fuels subject to higher taxes and detect tax evasion. Unscrupulous persons can make large profits simply by purchasing lower taxed fuels and selling them at the higher taxed fuel prices, or by diluting higher taxed fuels with lower taxed fuels and selling the diluted product again at the higher taxed fuel prices. C.I. Solvent Red 26 is currently used by the U.S. Internal Revenue Service to distinguish non-taxed home heating oil from other taxed fuels of identical composition yet used for different purposes, such as diesel motor fuel. If red dye is present, no federal taxes have been paid on the product. Presence of red color in the product is taken as evidence of tax evasion if the fuel is sold as taxed commercial diesel fuel.

Aside from tax matters, fuels are colored by major oil companies that market brand name products such as gasoline to prevent misuse by their dealers. Oil companies go to great expense to ensure their branded products meet stringent specifications regarding volatility and octane number, as well as to provide them with effective additive packages containing detergents and the like. Consumers rely upon the company's trademarks to assure themselves that the product being purchased is of high quality. Unscrupulous gasoline dealers can make large profits simply by diluting or substituting the brand name product with an inferior product and selling the resulting inferior product at the price consumers are willing to pay for the branded product. For example, it is possible for dealers to cheat by blending lower priced products such as kerosene, heating oil, or diesel fuel into regular grade gasoline or blending regular grade gasoline into higher priced premium gasoline and selling the inferior product at a premium price. Colored fuels thus provide oil companies with means to visually distinguish brand and grade denominations and police their dealers.

Another valuable function of fuel colorants is for identification of particular production batches of bulk liquids for protection against theft, particularly for identifying fuels owned by large government, military or commercial consumers. Fuels are also dyed so that oil companies can identify their branded products from others', particularly when faced with product warranty, product liability, and pollution claims.

Yet, it is also known that visible dyes, when used as fuel colorants, are not always reliable for tagging purposes. While it may be extremely difficult, it is not impossible for unauthorized persons to selectively remove visible dyes from the fuels. For instance, one form of deception in the past has been to decolorize non-taxed heating oil with absorbents, such as activated charcoal, and then sell the colorless product as higher priced diesel fuel. Another problem is that the color imparted by visible dyes may be obscured by natural substances or additives present in the fuels, making visual color recognition extremely difficult. High dosage levels (e.g., 25 to 100 ppm) are also needed for visual detection, which creates other problems, such as increased costs.

Because colorants alone have such shortcomings, there has been a growing desire to mark or tag fuels with, in addition to or in place of the dye colorant, markers or taggants that impart no visual coloration to the tagged product, yet are still detectable by a quick and simple chemical or physical test procedure. Markers that are not visually discernable to the unaided eye in the tagged product at the levels which they are used are termed "silent" markers or taggants. Silent markers, accordingly, identify a product only to an authorized tester and do not provide any visual indication of the identity of the product to the regular observer or those parties interested in violating brand or product integrity. Adulteration and misuse of fuels, therefore, becomes much more difficult. For instance, even if unscrupulous persons attempt to remove such markers to the point of non-detectability, they will never be able to determine whether their laundering efforts were successful without knowledge of the marker utilized or access to the authorized tester's detection equipment. Traditionally, there have only been relatively few silent markers available.

There are also a number of drawbacks associated with the currently available silent markers. Many require chemical manipulation of a fuel sample for detection which generates waste materials necessitating disposal. These markers are typically fuel soluble visible dye precursors which are virtually colorless compounds when employed at recommended dosage levels, yet are known to react with selected reagents to from intensely colored derivatives, as for example, as taught in U.S. Pat. No. 4,209,302 (Orelup). Chemical detection normally requires extraction of the marker with an acidic or basic aqueous liquid extractant, followed by addition of a reagent to cause the extract to turn a visibly distinct color, although in some cases, the reagent is unnecessary. While effective, this procedure has a couple of drawbacks. For instance, it is time-consuming to perform. It also does not provide a good quantitative measurement of marker concentration in the field. Quantitative determinations are particularly important in cases where dilution is suspected. For a rough estimate of marker level, inspectors in the field are given color charts against which to compare the developed color intensity to determine fuel identity and extent of dilution. However, laboratory verification is needed to confirm the marker concentration. Lastly, the tested by-products must be handled and disposed of as hazardous waste, which is manifestly cumbersome.

Truly silent markers which are not visible at any concentration have also been proposed for invisibly tagging petroleum products. These markers are typically large organic molecules that have virtually no absorbance in the visible portion of the spectrum and that absorb and/or fluoresce in the near infrared to mark their presence in a fuel sample. U.S. Pat. No. 5,525,516 (Krutak et al.) and European Patent 0,656,929 (Albert et al.) describe such markers. In these references, the presence of such a marker is detected in the fuel by exposing the fuel to near infrared radiation and then either detecting the characteristic light absorption spectra of the marker or its emitted fluorescent light in the near infrared region with standard absorption or fluorescent detection equipment. While the detection procedure is much simpler, molecules or markers that are active in near infrared are large, complex, organic structures. Therefore, these markers are difficult and expensive to make. Furthermore, there are only a finite number of near infrared absorbing or fluorescing molecules that can serve as silent markers, since many of these molecules absorb in the visible portion of the spectrum as well.

In sum, few practical markers exist and even fewer practical silent markers exist. Furthermore, many silent markers are expensive or not user friendly in that a user must chemically manipulate a fuel sample and handle and dispose of potentially hazardous chemicals. With the growing drive to prevent brand adulteration of fuels and to authenticate fuels, and the widening use of markers around the world for fiscal marking and enforcement of taxation, more silent markers and improved methods for invisibly marking and identifying petroleum products are needed.

Never before had one skilled in the art thought it possible to use visible dyes as silent markers, rather than as colorants, for liquid petroleum products until the present invention. This use of visible dyes by its very nature is highly unexpected.

SUMMARY OF THE INVENTION

The present invention provides a novel method for silently or invisibly marking or tagging, for subsequent identification purposes, a liquid petroleum hydrocarbon product by means of visible dyes, wherein the method comprises incorporating in the product, one or more visible dyes at levels which cannot be detected by the human eye, preferably about 1 ppm or less. The visible dyes useful in the practice of the present invention are selected from hydrocarbon-soluble compounds which have their absorption maximum ($\lambda$ max) in the higher portion of the visible spectrum over wavelengths from about 500 to 700 nm, preferably from about 550 to 700 nm. Preferably, the visible dyes are selected from the classes of anthraquinone dyes and azo dyes.

In a preferred aspect of the present invention, this method comprises incorporating in the product to be tagged, at levels which cannot be detected by the human eye, a mixture of two or more visible dyes of the aforesaid character which have their absorption maximum ($\lambda$ max) at differential wavelengths from each other as not to interfere with individual detection. In this aspect of the invention, the relative amount of dyes can be varied to generate multiple absorption patterns, which allows for the creation of a large family of silent markers merely from the repetitive use of a single set of dyes, greatly increasing the number of practical silent markers available.

The present invention also provides a method for identifying a petroleum product so tagged by exposing the product to visible radiation having wavelengths in the aforesaid portion of the visible spectrum utilized and detecting and quantifying the presence of the visible dyes from their absorption in this spectral region.

The present invention is quick and simple to perform, inexpensive, environmentally safe, requires minimal instrumentation, creates no chemical waste products for disposal, and gives true quantitative results in the field.

The present invention also provides novel visible dye compositions appropriate for said invisible tagging.

DETAILED DESCRIPTION OF CERTAIN PREFERRED EMBODIMENTS

Ideally, the visible dyes useful in the practice of the invention should possess the following properties:

1. high solubility in petroleum hydrocarbons to allow for easy dissolution and permit uniform detection throughout the tagged product;
2. permit use at extremely low levels so as to impart no visual coloration to the tagged product, e.g., 1 parts per million (volume/volume) ("ppm") or less;
3. still give a detectable absorption spectra at such extremely low levels with available visible spectrophotometers;
4. have a wavelength of maximum absorption ("$\lambda$ max") in the higher portion of the visible spectrum in the region from about 500 to 700 nanometers ("nm"), preferably from about 550 to 700 nm, to avoid interference from inherently strong background absorption of petroleum hydrocarbons;
5. have at least one characteristic wavelength region in the above utilized portion of the visible spectrum where the marker's absorption is differential from the background petroleum hydrocarbon as well as any other marker chemical or colorant present in the tagged product;
6. insolubility in water to prevent the dye from being leached out of the tagged hydrocarbon into the water phase often found in hydrocarbon storage tanks, for example, from condensation;
7. stability in the presence of components which are likely to be present in tagged hydrocarbons such as additives, for example, deposit control agents, antioxidants, detergents, etc.;
8. stability to ambient conditions, for example, to moisture, oxygenates, temperature, etc.;
9. capable of detection and quantification in a quick and simple manner by non-scientific personnel, without the need for potentially hazardous detection chemicals; and,
10. create no chemical waste products for disposal and be environmentally safe.

The visible dyes useful in the practice of this invention are preferably selected from the classes of anthraquinone dyes and diazo dyes.

Suitable anthraquinone dyes have, for example, the formula I

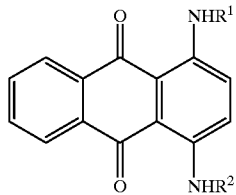

(I)

where $R^1$ and $R^2$, independently from one another, are each hydrogen or $C_1$–$C_{12}$ alkyl, where the alkyl groups may be interrupted by from 1 to 4 oxygen atoms or substituted with a phenyl or substituted phenyl.

Preferred anthraquinone dyes of formula I include, without limitation, the dyes of formulas II and III Automate® Blue 8 (C.I. Solvent Blue 98)

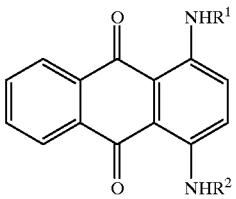

(II)

where $R^1$ and $R^2$ are a mixture of alkyl radicals which have the formulas

1) $R^1 = R^2 = CH_3$    4) $R^1 = CH_3, R_2 = C_5H_{11}$
2) $R^1 = R^2 = C_5H_{11}$  5) $R^1 = CH_3, R^2 = C_8H_{17}$
3) $R^1 = R^2 = C_8H_{17}$  6) $R^1 = C_5H_{11}, R^2 = C_8H_{17}$

λ max of 646 nm in iso-octane
Automate® Blue 9A (C.I. Solvent Blue 79)

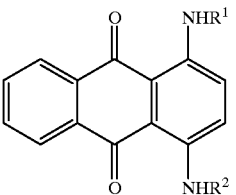

(III)

where $R^1$ and $R^2$ are a mixture of alkyl radicals which may be interrupted by one oxygen atom and have the formulas 1) $R^1 = R^2 = CH_3$    4) $R^1 = R^2 = C_3H_6OCH_3$
2) $R^1 = R^2 = C_5H_{11}$  5) $R^1 = CH_3, R^2 = C_5H_{11}$
3) $R^1 = R^2 = C_8H_{17}$  6) $R^1 = CH_3, R^2 = C_8H_{17}$
7) $R^1 = CH_3, R^2 = C_3H_6OCH_3$
8) $R^1 = C_5H_{11}, R^2 = C_8H_{17}$
9) $R^1 = C_5H_{11}, R^2 = C_3H_6OCH_3$
10) $R^1 = C_8H_{17}, R^2 = C_3H_6OCH_3$ λ max of 643 nm in iso-octane Suitable diazo dyes have, for example, the formula IV

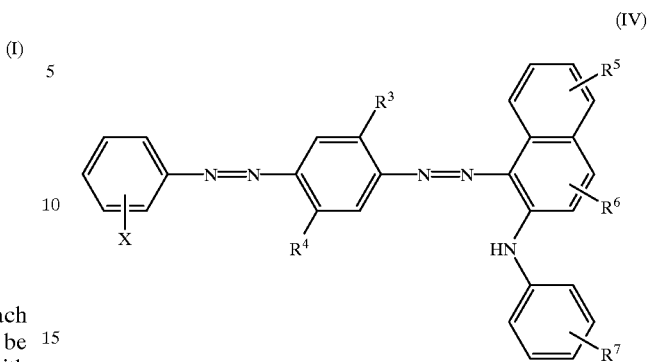

(IV)

where X is hydrogen or halogen, $R^3$ is hydrogen or $C_1$–$C_4$ alkoxy, $R^4$ is hydrogen or $C_1$–$C_4$ alkyl, $R^5$ and $R^6$, independently of one another, are hydrogen or $C_2$–$C_7$ alkenyl, and $R^7$ is hydrogen or $C_1$–$C_{12}$ alkyl.

Preferred diazo dyes of formula IV include, without limitation, the dyes of formulas V and VI Automate® Blue Black (C.I. Solvent Blue 99)

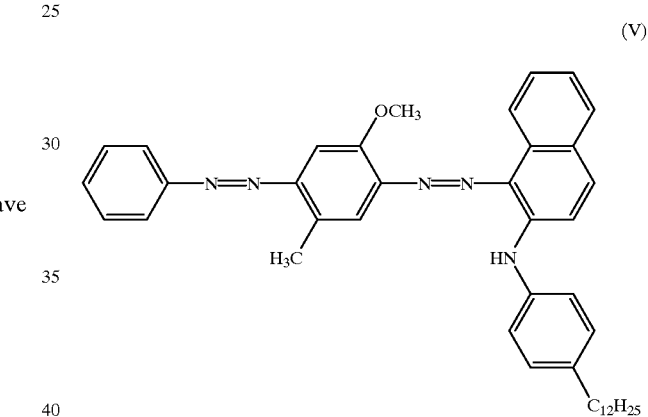

(V)

λ max of 564 nm in iso-octane,
Automates Blue 10 (C.I. Solvent Blue 100)

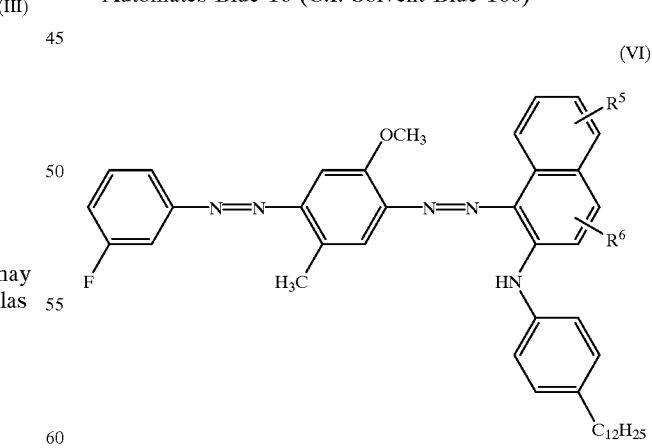

(VI)

where $R^5=R^6=C_7H_{13}$ or homologs
λ max of 578 nm in iso-octane

The specific Automate® dyes mentioned above are available from Morton International, Inc., located in Chicago, Ill.

The above compounds make it very simple to detect the markers from their characteristic absorption in the portion of the visible spectral region utilized, even if the marker substances are only present in minute quantities.

In a preferred aspect of this invention, as explained more fully below, novel dye mixtures of two or more aforesaid dyes which have their absorption maximum ($\lambda$ max) at differential wavelengths from each other as not to interfere with individual detection are employed. Using state of the art detection equipment, it is believed that such differences in the absorption maximum of as little as about 15–100 nm in wavelength can be discerned. Of course, this limitation is not critical and will decrease as detection methodology improves. Highly preferred novel dye mixtures of the present invention include at least one dye of formula I and at least one dye of formula IV. Specific examples of such mixtures include a dye of formulas II or III together with a dye of formula V or VI. Such dye mixtures enhance performance.

For tagging petroleum products, the visible dye or dye mixtures of the aforesaid character are preferably used in the form of solutions to facilitate handling, metering, blending and distribution in the petroleum product of interest. Suitable solvents include, without limitation, aromatic hydrocarbons, such as toluene, xylene, and other petroleum fractions, or any other which dissolve the dyes readily yet are not considered objectionable in the petroleum product. The aforesaid dyes are readily soluble in the stated solvents. However, in order to avoid the resulting solutions having excessively high viscosity, a total dye concentration of from about 25 to 50% by weight, based on the solution, is generally chosen.

In carrying out the method for invisibly tagging a petroleum product for subsequent identification purposes according to the present invention, one or more visible dyes of the aforesaid character, preferably in solution, are simply blended in a petroleum product to be tagged (or in any other organic liquid of interest in which these dyes are soluble) in a predetermined amount by conventional means. The blending can be accomplished by, for example, stirring, agitating, jet mixing, pumping, or recirculating the markers with the petroleum product. The dye concentration added may vary widely, depending upon several factors, including, but not limited to, particular dyes employed, particular petroleum products to be tagged, etc. However, it should be understood that it is critical to this invention that the dyes not exceed levels at which they can be detected by the human eye in the tagged product.

The preferred upper limit for each visible dye employed as a silent marker is typically about 1 ppm. Furthermore, the visible dyes are preferably added at the minimum concentration required to produce a characteristic absorption pattern, in the higher portion of the visible spectrum utilized, that is consistently detectable with conventional absorption detection equipment sensitive in this region. In general, as little as 0.1 ppm of the dye will be sufficient to produce a consistently detectable absorption pattern. Typically, each visible dye is added to a petroleum product in a level from about 0.4 to about 1.0 ppm.

It is also important that the dyes employed have their maximum absorption ($\lambda$ max) in the higher portion of the visible spectrum at wavelengths generally from about 500 to 700 nm, preferably from about 550 to 700 nm, since petroleum hydrocarbons, and in particular gasoline, have inherently strong interfering absorption in the lower portion of the visible spectrum, typically at wavelengths below 500 nm, arising from color bodies naturally present in petroleum hydrocarbons. This background absorption prevents the use of visible dyes which have a $\lambda$ max below about 500 nm, since higher concentrations (i.e., visually perceptible levels) are needed to produce a signature absorption that is differential from the background fuel. In contrast, the portion of the visible spectral region utilized herein is remarkably absorption free and provides an excellent region for the practice of the present invention.

In a preferred aspect of the present invention, it is desired to create multiple unique marking patterns from the repetitive use of a single dye or a mixture of dyes, which allows for the creation of a whole family of silent markers. In the case of a single dye, simply by varying the concentration (i.e., dosage level) of the dye employed in the tagged product, a number of differential marking patterns can be created. For example, a regular grade of gasoline can be invisibly tagged with a single dye at one predetermined concentration. While the same oil company's premium grade of gasoline can invisibly tagged with the same visible dye but at a different predetermined concentration. The identity of each liquid can therefore be encoded in a specific dye concentration. During gasoline production, this enables a refinery to quickly perform a quality check to determine whether the proper grade of gasoline is flowing through the pipeline.

In another preferred aspect of the present invention, novel dye mixtures containing two or more visible dyes of the aforesaid character which have their absorption maximum at differential wavelengths from each other as not to interfere with individual detection are used to invisibly tag petroleum products. Simply by varying either the concentration of the tagging mixture employed or the concentration ratios of the dyes employed in the mixture, a whole family of unique marking patterns can be created. The former case is similar to that described above for a single dye. In the latter case, for example, one liquid petroleum product of one company can be invisibly tagged with a dye mixture comprised of a first visible dye and a second visible dye, wherein the ratio of the concentration of the first dye to the second dye equals a predetermined value. While a second liquid petroleum product of another company can be tagged with the same visible dye mixture but at a different predetermined concentration ratio of first to second dye. In this manner, the identity of each liquid can be encoded in different combinations of the same two dyes. This enables use of the same markers by different oil companies without overlap or confusion.

The number of marking patterns that can be generated in the above methods is limited only by measurement sensitivity of the detection equipment. Usually, the dyes are employed in concentrations that are multiples of a selected basis concentration.

The present invention also provides a method for subsequently identifying a so tagged petroleum product by detecting the presence and quantity of the visible dyes directly in the tagged product from the, characteristic absorption pre-assigned to each dye in the portion of the visible spectrum utilized herein, i.e., between about 500–700 nm, preferably between about 550–700 nm. This method is advantageously non-destructive to the petroleum product, requires minimal instrumentation, and creates no hazardous waste products.

In carrying out this method, a petroleum hydrocarbon sample is exposed to visible radiation from a suitable light source having wavelengths over the marker's characteristic absorption region, followed by detection of the characteristic absorption by means of light absorption detection equipment capable of detecting absorption of the petroleum sample in this region to confirm the marker's presence. The concentration of the marker is measured directly in the tagged petroleum using this method, since according to Beer's law, the intensity of absorption is directly related to the concentration of the marker in the tagged product. Accordingly, this method which is afforded by the markers described herein is not only quick and simple to perform, but also is capable of providing true quantitative measurements of marker concentrations in the field.

It should be understood that any apparatus capable of detecting absorption in the range described herein may be used, such as commercially available visible spectrophotometers or calorimeters which are sensitive in this range.

Typically, the tagged petroleum hydrocarbon sample is placed in a transparent sample cell which is then inserted into a cell chamber of a detector. A light source housed in the detector is then used to irradiate the sample with visible radiation having wavelength outputs in the portion of the visible spectrum described herein. Wavelength selective filters are usually placed in front of the light source to isolate the wavelength outputs to the narrow band of visible radiation associated with the absorption which has determined to be characteristic of the markers assigned to the specific fuel of interest. Detectors capable of detecting absorption this region are located on the opposite side of the cell chamber. Typically, there is at least one detector assigned to each marker of interest.

It is also preferred that the detection equipment not only detect the presence of the dyes from their characteristic absorption signature, but also calculate dye concentrations from absorption data, calculate dye concentration ratios when dye mixtures are utilized, and compare the concentrations or concentration ratios found in a fuel sample with a table of preset values to assist in identifying the fuel and determining whether the fuel has been adulterated or counterfeited. It is also preferred that during operation the equipment produce a detection signal which gives rise to a visible readout or an appropriate alarm. Suitable detectors capable of providing direct readout information of marker concentrations, concentration ratios, and fuel identity in the field are more fully described in U.S. Pat. No. 5,225,679, which is incorporated by reference herein in its entirety. Examples of commercially available equipment which provides such instant verification of the nature of a fuel sample in the field, include a PetroSpec® analyzer available from Boston Advanced Technologies, Inc., located in Marlborough, Mass. or a SpecTrace™ analyzer, available from Morton International, Inc., located in Chicago, Ill., both being outfitted with optical filters appropriate for the markers assigned to the particular fuels of interest.

This equipment houses an on-board computer processor and control unit to drive the lamp, receive and process the detection signals from the detectors, and display numerical, textual, or graphical read out information concerning the fuel identity at display units located on the external surface of the apparatus. For example, the computer processor and control unit can be programmed to calculate and display the concentration of the marker or markers from the amount of absorbance in the characteristic region, the marker concentration ratios if multiple markers are used, and compare the measured marker concentration or ratio of the measured concentrations with a table of predetermined values which stores information about marking patterns (i.e., concentration or concentration ratios) and fuels assigned to each marking patterns and displays information concerning the fuel identity, counterfeiting, or amount of fuel adulteration.

With this detection method, petroleum products which have been invisibly tagged in the manner described above either with different levels of the same visible dye or dye mixtures or with different combinations of dyes in a mixture and then detected according to the method of the present invention, unique marking patterns are revealed for each variation, despite the repetitive use of the same dye or dye mixtures. For example, where two different grades of gasoline are separately tagged with different levels of a single dye, by measuring the exact concentration of the single dye directly in the fuel and comparing the measured concentration with the preassigned values assigned to the particular fuel of interest, a fuel can be easily identified. Any significant deviation from the expected marking pattern (i.e., concentration) alerts the operator to the potential presence of another fuel therein. Dye mixtures can also be employed and detected in a manner similar to that described above for a single dye. Dye mixtures can also be employed in a different manner. For instance, where different brands of fuels are tagged with different combinations of the same dye mixture, by measuring the concentrations of the dyes and comparing the ratio of the measured concentrations with the predetermined values assigned to the particular fuel of interest, a fuel can be easily identified as well. For example, when testing for a particular brand of petroleum, if upon measurement, the product is found to have first and second dye concentrations equal to a ratio preassigned to this brand, the product is identified as authentic. If the product is found not to have the preassigned ratio of dyes, the product is identified as not authentic and perhaps as adulterated.

Since the detection method does not involve chemical manipulation of the fuel, after the sample has been tested, it may be returned to its original source, eliminating the need for handling and disposal of hazardous chemicals.

The invention will now be described in greater detail by way of specific examples. All parts and percentages specified therein are by weight unless otherwise indicated.

EXAMPLE 1

A diesel fuel purchased from a local dealer was tagged with a dye solution of the following composition containing a single dye:

35.000±0.01 grams of a 55% strength solution of the dye of formula V in xylene;

65.000±0.01 grams of xylene.

The dye solution was added to a 150 ml flask and stirred for a period of 15–20 minutes to ensure homogeneity.

2.66, 2.00, 1.80, 1.60, 1.40, 1.20, 1.00, 0.80, and 0.60 mg of the stated mixture were added per liter of the stated gasoline. After the fuels had been tagged at the stated concentration, in none of them could the dye be detected by the human eye.

To detect the presence of the dye in the tagged product, each tagged product was poured into a sample cell and analyzed at the using a SpecTrace™ analyzer.

The dye content was determined quantitatively by spectrometric measurement with the SpecTrace™ analyzer programmed to detect absorption at specific wavelengths of 550 nm, 580 nm, 620 nm, 656 nm and 700 nm (base line).

During detection, the analyzer first verifies the presence of the dye by detecting the specific absorption pattern which has been assigned to be characteristic of the dye at the above wavelengths. If the dye is present, the read out will be "I.D. Confirmed". The dye concentration is also measured and displayed. In the instant example, the analyzer was programmed such that a 2.00 mg/l concentration of the marker would give a read out of 100.0%. Significant deviations from 100%, such as greater than 20% deviation, is indicative of possible adulteration and the extent of adulteration. Following were readings obtained for the above solutions.

| Marker Concentration (mg/l) | SpecTrace ™ I.D. | Readout Concentration, % | Expected Readout |
|---|---|---|---|
| 2.66 | Confirmed | 192.6 | 133.0 |
| 2.00 | Confirmed | 100.1 | 100.0 |
| 1.80 | Confirmed | 90.3 | 90.0 |
| 1.60 | Confirmed | 80.0 | 80.0 |
| 1.40 | Confirmed | 70.1 | 70.0 |
| 1.20 | Confirmed | 59.7 | 60.0 |
| 1.00 | Confirmed | 50.0 | 50.0 |
| 0.80 | Confirmed | 39.3 | 40.0 |
| 0.60 | Confirmed | 31.0 | 30.0 |

The treat rates in the above Table are such that it allows detection and quantification of the markers when one part of marked fuel is adulterated with as much as four parts of unmarked fuel.

EXAMPLE 2

A Mobil brand of regular unleaded gasoline was tagged with a dye solution of the following composition containing a mixture of two dyes, wherein the two tagging dyes contained in the mixture are provided in a ratio of about 1:1 by weight:

15.000±0.01 grams of a 59% strength solution of the dye of formula 11 in xylene;

15.000±0.01 grams of a 55% strength solution of the dye of formula V; and, 30.000±0.01 grams of Aromatic 200 solvent.

The dye solution was added to a 100 ml flask and stirred for a period of 15–20 minutes to ensure homogeneity.

2.66, 2.00, 1.80, 1.60, 1.40, 1.20, 1.00, 0.80, and 0.60 mg of the stated mixture were added per liter of the stated gasoline. After the fuels had been tagged at the stated concentration, none of the dyes could be detected by the human eye.

To detect the presence of the two dyes in the tagged products, each tagged product was then poured into a sample cell and analyzed using the SpecTrace™ Analyzer programmed to read absorption at the wavelengths stated in Example 1 which are characteristic of the dyes.

During detection, the analyzer first verifies the ratio of the two dyes from their characteristic marking pattern assigned to the dye mixture. If the ratio is correct, the read out will be "I.D. Confirmed". The concentration ratios of the two dyes are also displayed. In the instant example, the analyzer was programmed such that a 2.00 mg/l concentration of the marker would give a read out of 100.0%. Following were readings obtained for the above solutions.

| Marker Concentration (mg/l) | SpecTrace ™ I.D. | Readout Concentration, % | Expected Readout |
|---|---|---|---|
| 2.66 | Confirmed | 133.2 | 133.0 |
| 2.00 | Confirmed | 99.9 | 100.0 |
| 1.80 | Confirmed | 90.0 | 90.0 |
| 1.60 | Confirmed | 80.4 | 80.0 |
| 1.40 | Confirmed | 69.5 | 70.0 |
| 1.20 | Confirmed | 60.8 | 60.0 |
| 1.00 | Confirmed | 49.7 | 50.0 |
| 0.80 | Confirmed | 40.7 | 40.0 |
| 0.60 | Confirmed | 31.1 | 30.0 |

The above approach can be generalized to other dye combinations to create a family of silent markers. For example, the above dye mixtures can be employed in multiples of the 1:1 concentration ratios, such as 1:2, 1:1, 2:1, providing three detectably different marking patterns which can be used to uniquely mark three different petroleum products. The number of marking patterns is limited only by the sensitivity of the detection equipment.

In sum, the present invention provides a means to invisibly tag fuels very simply and relatively inexpensively and to detect the so tagged fuels while remarkably using visible dyes at levels invisible to the human eye, yet which are still detectable by quick and simple methods that require minimal instrumentation, produce no chemical waste products, and give quantitative results in the field.

From the foregoing it will be seen that this invention is one well adapted to attain all ends and objects hereinabove set forth together with the other advantages which are apparent and inherent. Since many possible variations may be made of the invention without departing from the scope thereof, the invention is not intended to be limited to the embodiments and examples disclosed, which are considered to be purely exemplary. Accordingly, reference should be made to the appended claims to assess the true spirit and scope of the invention, in which exclusive rights are claimed.

What is claimed is:

1. A method for identifying an invisibly tagged liquid petroleum hydrocarbon, comprising:

exposing a petroleum hydrocarbon to visible radiation having wavelengths of about 500 to about 700 nm, wherein said petroleum hydrocarbon has incorporated therein dyes consisting essentially of at least one anthraquinone dye and at least one diazo dye, each at a level below 1 ppm, wherein the dyes are hydrocarbon-soluble, and wherein the dyes have their absorption maximum in the visible spectrum over wavelengths from about 500 to about 700 nm; and, detecting the presence of the dyes from their absorption in a wavelength region from about 500 to about 700 nm without performing any chemical manipulation of the petroleum hydrocarbon.

2. The method of claim 1, wherein the petroleum hydrocarbon is selected from the group consisting of gasoline, jet fuel, diesel fuel, heating oil, and kerosene.

3. The method of claim 1, wherein said at least one anthraquinone dye and at least one diazo dye have their absorption maximum in the visible spectrum in the wavelength range from about 550 to about 700 nm and exposure is over said wavelength range.

* * * * *